United States Patent [19]
Ponce de León et al.

[11] Patent Number: 6,156,569
[45] Date of Patent: Dec. 5, 2000

[54] PROLONGED CULTURING OF AVIAN PRIMORDIAL GERM CELLS (PGCS) USING SPECIFIC GROWTH FACTORS, USE THEREOF TO PRODUCE CHIMERIC AVIANS

[75] Inventors: F. Abel Ponce de León, St. Paul, Minn.; Catherine Blackwell, Warren, Mass.; Xiu Ying Gao, S. Deerfield, Mass.; James M. Robl; Steven L. Stice, both of Belchertown, Mass.; D. Joseph Jerry, Shutesbury, Mass.

[73] Assignee: University of Massachusetts Office of Vice Chancellor for Research at Amherst, Amherst, Mass.

[21] Appl. No.: 08/905,773

[22] Filed: Aug. 4, 1997

[51] Int. Cl.[7] .............................. C12N 15/85; C12N 5/00; A01K 67/00
[52] U.S. Cl. ......................... 435/349; 435/377; 435/325; 800/21; 800/8
[58] Field of Search .................................. 800/8, 19, 21; 435/325, 349, 377

[56] References Cited

U.S. PATENT DOCUMENTS 5,759,763 6/1998 Naito et al. ............................... 435/1.1

OTHER PUBLICATIONS

Pain et al. Long–term in vitro Culture and Characterisation of Avian Embryonic Stem Cells with Multiple Morphogenic Potentialities. Development, vol. 122, pp. 2339–2348, Aug. 1996.

Sang, H. Transgenic Chickens–Methods and Potential Application. TIBTECH, vol. 12, pp. 415–420, Oct. 1994.

Maclean, N. (Ed.), Animals with Novel Genes. Simkiss, K. Transgenic birds. University Press. pp. 106–137, 1994.

Alberts et al. (Ed.). Molecular Biology of The Cell. Garland Press. p. 162, 1989.

*Primary Examiner*—Bruce R Campell
*Assistant Examiner*—Deborah J. R. Clark
*Attorney, Agent, or Firm*—Burns, Doane, Swecker & Mathis, LLP

[57] ABSTRACT

A culture system for maintaining avian PGCs for long periods in tissue culture is provided. This culture system uses LIF, bFGF, IGF and SCF. The resultant PGCs are useful for the production of transgenic and chimeric avians, in particular, chickens or turkeys.

12 Claims, No Drawings

PROLONGED CULTURING OF AVIAN PRIMORDIAL GERM CELLS (PGCS) USING SPECIFIC GROWTH FACTORS, USE THEREOF TO PRODUCE CHIMERIC AVIANS

FIELD OF THE INVENTION

The present invention provides a novel method for maintaining avian primordial germ cells (PGCs), in particular chicken PGCs, for prolonged periods in tissue culture. These PGCs can be used for the insertion of desired DNA sequences, e.g., human genes. These cultured PGCs, and transgenic PGCs derived therefrom, may be used to produce chimeric birds, in particular chimeric chickens.

BACKGROUND OF THE INVENTION

In recent years there has been much research focused toward the production of chimeric, cloned and transgenic animals.

In particular, the modification of the genome of farm animal species is an area which has been actively pursued, with varying degrees of success, for the past two decades. For example, such research has been focused toward generating transgenic pigs, cows, and chickens. To date, the majority of the available transgenic animals have been generated by the direct microinjection of single cell embryos with DNA constructs harboring the gene of interest. However, while microinjection techniques have been successful, such methods are disadvantageous in that they are costly and often suffer from low efficiency.

Recently, the success of embryonic stem (ES) cell technology for the production of "knock-out" mice has led to research focused toward the development of tissue culture systems for ES cells and primordial germ cells (PGCs) in farm animal species. The ability to maintain ES undifferentiated cells in continuous culture enables in vitro transfection of such cells and ideally the selection of transfected cells which contain a desired gene prior to their transfer to the inner cell mass of a developing embryo to generate chimeric animals. Ideally, at least some of the resultant chimeric animals will be able to segregate the DNA construct via the germ line and, hence, produce transgenic progeny. However, to date, targeted (site-specific) integrations have only been achieved in mice. Currently, the ability to do targeted DNA integration in other animal species is limited. However, work in this direction is in progress and should be realized soon.

In particular, there has been considerable research targeted toward improving the genome of Gallinacea and chickens in particular because of the considerable economic importance thereof. A fairly complete review of the state of research directed at the generation of transgenic chickens was published three years ago (Sang, *Trends in Biotech.*, 12: 415–420 (1994)). As discussed therein, there are basically two alternative routes under investigation for producing transgenic chickens. These methods can be distinguished based on the time when manipulation of the genome is effected, i.e., before lay or after lay. The latter method includes the transfer of donor ES and PGC to recipient embryos. Moreover, in both routes, the bulk of the work has been effected by infecting donor cells with retroviral vectors containing a gene of interest.

The first approach, which comprises manipulation of the genome before lay has yielded mixed and/or inefficient results. For example, the infection of oocytes in the ovary (Shuman, and Shoffner, *Poultry Sci.*, 65: 1437–1494 (1986) and pre-incubation of sperm with plasmid DNA (Gruenbaum et al., *J. Cell. Biochem Supp.*, 15: 194 (1991) were inefficient and have not been repeated. Also, the transfection of sperm cells with a plasmid construct by lipofection has been demonstrated (Squires and Drake, *Anim. Biotech.*, 4: 71–78 1993). However, germ line transmission was not reported.

Also, the direct microinjection of DNA into the germinal disk followed by embryo culture has been reported to yield 0.1% live transgenic chimeric birds (Sang, W., *Trends in Biotech.*, 12: 415–42 (1994)) with one bird transmitting the transgene to 3.4% of its offspring (Love et al., *Bio/Technology*, 12: 60–63 (1994)). This same approach was taken by Naito et al (*J. Reprod. Fertil.*, 102: 321–325 (1994)). However, similarly no germ line transmission of the transgene was reported therein.

The second approach, which comprises manipulation of the genome after lay, has yielded better results. Chimeric birds, generated by injection of laid eggs with replication competent retroviral vectors, have shown germ line transmission to 1% and 11% of their offspring (Salter et al., *In Manipulation of the Avian Genome*, Etches, R J et al., eds. pp 138–150 CRC Press (1993)). More encouraging results, using replication-defective retroviral vectors and injection into laid eggs, generated 8% chimeric male birds that transmitted the vector to their offspring at a frequency of 2 to 8% (Bosselman et al., *Science*, 243: 535–535 (1989)).

However, the injection of laid eggs with plasmid constructs in the presence of reagents known to promote transfection has failed to yield stably integrated or constructs or transgenic birds (Rosenblum and Cheng, J., *Cell Biochem Supp.*, 15E 208 (1991)). In general, the use of retroviral vectors for the generation of transgenic chickens is not widespread because of significant disadvantages associated therewith. Such disadvantages include the constraints on the size of the cloning insert that can be stably introduced therein and the more serious potential disadvantage of possibly inducing recombination events with endogenous viral loci or with other avian leukosis viruses.

A significant problem with all of these methods is the fact that long term culture systems for chicken ES and PGC have been relatively difficult to establish. To the best of the inventors' knowledge, it is believed that the longest avian PGCs have been cultured with the successful production of chimeric birds is less than 5 days.

Previous PGC culturing methods have included the use of growth factor, in particular LIF or IGF. However, as noted, such methods have not been able to provide for prolonged culturing periods, a prevalent concern as it would facilitate the production of transgenic PGCs.

Notwithstanding the problems in achieving long term culturing, both ES and PGC cells have been successfully used to generate chimeras by infection of such cells with replication competent and incompetent retroviral vectors. Further, as discussed above, freshly obtained blastodermal cells have been injected into recipient embryos, resulting in birds with chimeric gonads (Carsience et al., *Devel.*, 117: 669–675 1993)). Blastodermal cells can be efficiently transfected by lipofection and then transferred into recipient embryos. However, germ line transmission of transfected cells has not been reported.

Also, Pain et al., *Devel.*, 122: 2329–2398 (1996), have recently demonstrated the presence of putative chicken ES cells obtained from blastodermal cells. They further reported maintenance of these cells in cultures for 35 passages assertedly without loss of the ES phenotype (as defined by monoclonal antibodies to mouse ES cells). (Id.) These cells apparently develop into PGC's upon transfer into avian embryos where they colonize in the gonads. However, they did not establish definitively that these cells were in fact ES cells.

The cross-reactivity of mouse ES monoclonal antibodies with chicken ES cells might argue favorably for conservation of ES cell receptors across species. Also, the fact that these researchers were also able to generate two chimeric chickens with injections of 7 day old blastodermal cell cultures would arguably suggest the presence of ES cells in their system. However, these researchers did not rule out the possibility that PGCs were present in their complex culture system. Thus, this long term ES culture system should be further tested for pluripotency and germ line transmission. (Id.)

An alternative route to the production of ES cells, comprises PGCs. Procedures for the isolation and transfer of PGCs from donor to recipient embryos have been developed and have successfully generated chimeric chicken with germ line transmission of the donor genotype (Vick et al., *London Ser. B*, 251: 179–182 (1993), Tajima et al., *Theriogenology*, 40: 509–519 (1993)). Further, PGCs have been cryopreserved and later thawed to generate chimeric birds (Naito et al., *J. Reprod. Fertil.*, 102: 321–325 (1994)). However, this system is very labor intensive and only yields, on average, only 50 to 80 PGCs per embryo. Infection of PGCs with retroviral vectors has also been reported. However, to date, the growth of PGCs in culture for prolonged periods to facilitate selection of transfected PGCs has not been achieved. Thus, based on the foregoing, it is clear that improved methods for culturing PGCs comprises a significant need in the art.

OBJECTS OF THE INVENTION

It is an object of the invention to solve the problems of the prior art.

It is a more specific object of the invention to provide a novel method for culturing avian primordial germ cells (PGCs) for prolonged periods in tissue culture.

It is an even more specific object of the invention to provide a novel method for culturing Gallinacea, especially chicken, primordial germ cells (PGCS) for prolonged periods in tissue culture.

It is another object of the invention to use avian primordial germ cells which have been cultured for prolonged periods in tissue culture for the production of chimeric avians, preferably poultry, and most preferably chickens or turkeys.

It is another object of the invention to introduce desired nucleic acid sequences into avian primordial germ cells which have been cultured for prolonged periods in tissue culture.

It is yet another object of the invention to use avian primordial germ cells, which have been maintained in culture for prolonged periods, into which a desired nucleic acid sequence has been introduced, for the production of transgenic chimeric avians, preferably transgenic chimeric chickens or turkeys.

It is still another object of the invention to use such transgenic chimeric avians, preferably Gallinacea and most preferably chickens, for the production of heterologous protein(s) encoded by a nucleic acid sequence contained in cells introduced therein, preferably by recovery of such protein(s) from the eggs of such transgenic chimeric avians, in particular transgenic chimeric chickens. Alternatively, such proteins may be obtained from the chimeric bird directly, e.g., isolated from the blood or other tissues.

BRIEF DESCRIPTION OF THE INVENTION

As discussed, the present invention provides a novel method for maintaining avian (chicken) primordial germ cells (PGCs) in tissue culture for prolonged periods, i.e., for at least 14 days, more preferably at least 25 days, and ideally indefinitely.

Prior to the present invention, there were not reported any methods for maintaining avian PGCs in tissue culture which provided for their maintenance for longer than about 5 days (as demonstrated by their ability to produce chimeric avians). The present inventors have surprisingly discovered, by judicious experimentation, that the use of a culture media containing at the least the following growth factors: leukemia inhibitory factor (LIF), basic fibroblast growth factor (bFGF), stem cell factor (SCF) and insulin-like growth factor (IGF) enables avian primordial germ cells, specifically chicken primordial germ cells to be maintained and to proliferate for prolonged periods, i.e., at least 14 days, and for substantially longer in tissue culture. Moreover, these PGCs have been demonstrated to be useful for the generation of chimeric chickens.

Also, these PGCs should be useful for the production of transgenic avian PGCs, which can be used to produce transgenic chimeric avians. It is expected that these transgenic chimeric avians will be useful for recovery of heterologous proteins, which preferably can be recovered directly from the eggs of such chimeric transgenic avians. For example, such avians can be used for the production and recovery of therapeutic proteins and other polypeptides.

DETAILED DESCRIPTION OF THE INVENTION

Thus, the present invention obviates the problems associated with previous avian PGC culturing methods which did not enable such PGCs to be maintained in tissue culture for periods longer than about five days. In particular, the present inventors have surprisingly discovered that avian PGCs, preferably Gallinacea PGCs, and most preferably chicken PGCs can be maintained in tissue culture for prolonged periods, in at least 14 days, more preferably at least 25 days, and preferably longer, by the use of culture medium which contains at least the following four growth factors:

leukemia inhibiting factor (LIF), stem cell factor (SCF), insulin-like growth factor (IGF) and basic fibroblast growth factor (bFGF).

In general, the present culturing method comprises the following steps:

(i) isolating PGCs from donor avian embryos; and
  (ii) culturing said isolated avian PGCs in a culture medium containing relative amounts of LIF, bFGF, SCF and IGF effective to promote their proliferation, for a prolonged time, i.e., at least 14 days, in tissue culture. Prolonged periods, as defined above, refers to a culture period 14 days or longer.

Methods for isolation of primordial germ cells from donor avian embryos have been reported in the literature and can be effected by one skilled in the art. (See, e.g., JP 924997 published Sep. 7, 1993 Pub. No. 05-227947; Chang et al., *Cell Biol. Int.*, 19(2): 143–149 (1992); Naito et al., *Mol. Reprod. Devel.*, 39: 153–161 (1994); Yasuda et al., *J.*

Reprod. Fert., 96: 521–528 (1992); and Chang et al., Cell Biol. Int. Reporter, 16(9): 853–857 (1992), all of which are incorporated by reference in their entirety therein).

The present inventors elected to isolate avian PGCs from chicken eggs which had been incubated for about 53 hours (stage 12–14 of embryonic development), removal of embryos therefrom, collection of embryonic blood from the dorsal aorta thereof, and transferral thereof to suitable cell culture medium (M199 medium). These PGCs were then purified by ficoll density centrifugation, and resuspended in 10 μl of the growth factor containing culture medium of the present invention. However, as discussed above, other methods for isolating PGCs are known and may alternatively be used.

The isolated PGCs are then counted and separated manually (e.g., using a pipette). Thereafter, PGCs collected from these different avian embryos are pooled (to increase PGC numbers) and incubated in the subject growth factor containing medium.

This culture medium, hereinafter referred to as "complete" medium contains LIF, bFGF, SCF and IGF as well as other substituents typically comprised in PGC and embryonic stem cell medium. More specifically, the subject "complete" medium will preferably comprise α-MEM, a well known commercially available cell growth medium to which has been added the above four growth factors and which additionally includes 10% fetal calf serum, 2 mM L-glutamine, 0.56% antibiotic/antimitotic, 34.56 mM 2-β mercaptoethanol, 0.00625 U/μl of LIF, 0.25 pg/μl of bFGF, 0.5625 pg/μl of IGF and 4.0 pg/μl of SCF.

Based on the experiments conducted to date, these are believed to correspond to the minimal concentrations of these growth factors. However, as described infra, the amounts of these growth factors have been doubled with PGCs being successfully maintained in tissue culture. Thus, it is known that the respective amounts of these growth factors may be increased with no adverse effects. Moreover, even these minimum amounts may vary, e.g., if PGCs of other avians are cultured.

As noted, the present inventors used as the base medium, α-MEM, a well known commercially available tissue culture medium. However, it is expected that other media may be substituted therefor, provided that these four essential growth factors are also present. Applicants particularly contemplate modification of the subject "complete media" to eliminate fetal calf serum, because of its undefined and variable composition.

Also, while applicants cultured PGCs in the absence of feeder cells, they further contemplate that feeder cells may also be useful. In particular, the use of fibroblasts, preferably avian fibroblasts, and most preferably Gallinacea fibroblasts (still more preferably chicken fibroblasts), will provide for maintenance of PGCs in tissue culture provided that the four essential growth factors are present. Moreover, these feeder cells may be transfected with genes encoding these growth factors, thereby eliminating the need for the exogenous addition of these factors during culturing. Essentially, the cells will provide a continual source of these growth factors. (This will be achieved by placing these growth factor genes under control of constitutive strong promoter and also sequences that provide for the secretion thereof, thereby making these growth factors available to cultured PGCs.)

As noted, the amounts of these factors refer to relative amounts thereof effective to enable prolonged culturing of avian PGCs, preferably Gallinacea PGCs, and most preferably chicken or turkey PGCs, for prolonged periods in tissue culture.

Preferably, the relative amounts of these growth factors will fall within the following ranges:

LIF 0.00625 μ/μl to 0.625 μ/μl, more preferably 0.00625 to 0.0625 μ/μl and most preferably 0.00625 to 0.01250 μ/μl;

IGF 0.5625 pg/μl to 56.25 pg/μl, more preferably 0.5625 pg/μl to 5.625 pg/μl by weight and most preferably 0.5625 pg/μl to 1.125 pg/μl;

SCF 4.0 pg/μl to 400 pg/μl by weight, more preferably 4.0 pg/μl to 40 pg/μl and most preferably 4.0 pg/μl to 8.0 pg/μl by weight; and bFGF 0.25 pg/μl to 25 pg/μl, more preferably 0.25 pg/μl to 2.5 pg/μl by weight and most preferably 0.25 pg/μl to 0.5 pg/μl.

In the ranges set forth above, the upper ranges are not critical to the invention and are largely dictated by cost (given the significant expense associated with manufacture of growth factors).

However, it is expected that these preferred ranges may vary, e.g., if α-MEM is substituted by another growth medium and if other types of avian PGCs are cultured.

As discussed, these PGCs can be maintained for long periods in culture with the successful production of chimeric avians. To date, the cells have been maintained in tissue culture for up to about 4 months, with apparently no adverse effects. Also, cells of up to 25 days have been tested for their ability to effectively colonize avian embryonic gonads and produce chimeric birds. However, it is expected that these cells can be cultured indefinitely, with retention of the ability to produce chimeric birds.

Methods for using PGCs to produce chimeras are known in the art as evidenced by the prior art discussed supra. Preferably, PGCs will be transferred into recipient avian embryos according to the methods disclosed in the example while follows. Thereafter, successful chimera production is evaluated based on migration and colonization of PGCs in the gonads, retention of PGC phenotype, or by evaluating for the presence of donor PGCs in gonads after hatching and breeding.

In the present example, the inventors selected genotypes which are easily followed which affect coloration. Donor birds were white broiler type and recipient birds were black feathered birds, respectively, having specific potential genotypes. The putative chimeras were black feathered and produced black/white progeny when mated with black birds. Thereby, successful chimeras were demonstrated based on the production of black/white feathered progeny produced after mating the putative chimeric bird with another black feathered bird.

In a second strategy Bar Rock birds were used as recipients, and white feathered birds used as donors. Putative chimeric birds were demonstrated based on the production of white feathered progeny having some barred feathers.

However, the subject method should be applicable for introducing any desired trait by chimerization. This will, of course, depend on the genotypic properties of the transferred PGCs.

As discussed, a significant application of the subject PGCs, which can be maintained in culture for long periods, is for the production of chimeric avians. This will be accomplished by introducing a desired DNA sequence into the cultured PGCs. Means for introducing DNAs into recipient cells are known and include lipofection, transfection, microinjection, transformation, microprojectic techniques, etc. In particular, the present inventors initially elected to introduce a vector containing a reporter gene by lipofection. However, while transiently transfected PGCs were produced, a stable transfected cell line has not, as yet, been isolated. However, it is expected that this can be accomplished by known techniques using the subject PGCs.

Preferably, a DNA will be introduced that encodes a desired gene, e.g., therapeutic polypeptide, growth factor, enzyme, etc., under the regulatory control of sequences operable in avians. Preferably, these regulatory sequences will be of eukaryotic origin, most preferably avian, e.g., chicken regulatory sequences. Promoters operable in avian cells, e.g., derived from avian genes or viruses are known in the art.

Initially, a stable cell line which produces the desired protein will be isolated and used for chimera production. Also, it is desirable that the introduced DNA contain a marker DNA, the expression of which is easily detected, to more easily identify cells containing the inserted DNA. Such selectable markers are well known and include β-lactamase, β-galactosidase, neomycin phosphotransferase, etc.

Injection of the resultant transgenic PGCs into avian embryos will then result in the production of transgenic chimeric avians. Preferably, the desired protein will then be recovered from the eggs of these transgenic avians, thereby providing a continual supply of the protein. Alternatively, the protein can be recovered from chimeric birds directly, e.g., isolated from the systemic circulatory system.

EXAMPLE

The following materials and methods were used in the experiments described below.

Materials and Methods

Animals

White (E/E and I/I) broiler type chickens have been used as donors of PGCs to develop the long term PGC culture system. Two types of bird were used as recipient embryos, a dominant black feather (E/– and i/i) chicken line and a Bar Rock (E/E and i/i) line. Dominant black birds injected with white broiler (WB) type PGCs are referred as E/–(WB) and Bar Rock birds injected with white broiler type PGCs are referred as BR(WB).

Extraction of PGCs

Stage 13 to 14 embryos were selected for PGC extraction. PGCs were collected from the dorsal aorta with a fine micropipette as described by Naito et al., *Mol. Reprod. Dev.*, 37: 167–171 (1994). PGCs from 20 embryos were pooled in Hanks' solution supplemented with 10% fetal bovine serum and concentrated by Ficoll density gradient centrifugation (Naito et al., *Mol. Reprod. Dev.*, 39: 153–171 1994). PGCs were counted and distributed in 10 µl drops of culture medium (DMEM, containing differing amounts of growth factors) at about 100 PGCs per drop. Culture drops were overlaid with sterile light mineral oil.

Injection of PGCs Into Recipient Embryos

Stage 14–15 embryos were used as recipient embryos. After placing the egg on an appropriate surface, time was allowed for the developing embryo to position itself on the upper side of the resting egg. A small, about 10 mm "window" or less in the shell was made with a fine forceps. The embryo was brought close to the surface by adding a mixture of phosphate buffer saline with 4% antibiotics. After accommodating the embryo to visualize its heart, the marginal vein and/or dorsal aorta could be easily identified. Two hundred donor PGCs in 2 µl of media containing 0.04% trypan blue were taken into a micropipette. PGCs were injected into the dorsal aorta of the recipient embryo. Trypan blue, an inert cell dye, allowed visualization of the PGC suspension when it was being delivered. After injection the egg shell opening was closed with surgical tape and reinforced with paraffin. Eggs were maintained for 24 hours under surveillance in a humidified CO2 incubator and later transfer to a regular incubator until hatching.

Viable Fluorescent Staining of PGCs

To evaluate the success of transfers and/or the ability of PGCs to migrate to the gonads, PGCs were stained with DiI fluorescent stain. Embryos were collected after 24 hours of transfer, placed on a petri-dish and observed under an inverted microscope equipped for epi-fluorescent analysis.

PGC Culture Conditions

Several concentrations of human leukemia inhibitory factor (Lif), human basic fibroblast growth factor (bFGF), human insulin-like growth factor (IGF) and human stem cell factor (SCF) have been tested. Likewise, mitomycin treated chicken fibroblast and mouse STO cell feeder layers were tested.

PGCS Long-Term Cell Culture Medium

The complete cell culture medium is made of α-MEM, 10% fetal calf serum, 2 mM L-glutamine, 0.56% antibiotic/antimitotic, 34.56 mM 2-β mercaptoethanol, 0.00625 U/µl of leukemia inhibitory factor (LIF), 0.25 pg/µl of basic fibroblast growth factor (b-FGF), 0.5625 pg/µl of insulin like growth factor (IGF) and 4.0 pg/µl of stem cell factor (SCF). Medium changes were carried out every other day by removing 5 µl of medium and adding 5 µl of 2× new medium. The latter assumed that growth factors will be labile after some period of continuous culture. However, the net result is that the concentration of growth factors is doubled. Hence, the final medium contains now the following growth factor concentrations: 0.0125 U/µl of leukemia inhibitory factor (LIF), 0.5 pg/µl of basic fibroblast growth factor (bFGF), 1.125 pg/µl of insulin like growth factor (IGF) and 8.0 pg/µl of stem cell factor (SCF). The range of growth factor concentrations described here promote the maintenance and proliferation of PGCs in continuous culture. However, PGCs survive and proliferate better at the highest end of the described growth factor concentrations.

Using these culturing conditions, PGCs form large, dense, loosely adherent clumps of cells (some of the clumps have several hundreds of cells in them) within 3 to 4 days after collection. At the end of 7 days the clumps start to have large numbers of dead cells and cellular debris surrounding them. PGC clumps survive up to four weeks before they become cell monolayers. At weeks 1, 2 and 3, clumps have been dissociated, stained with a vital dye DiI and transferred into recipient embryos. At all three time-points cells were found in the gonads of some of the recipient embryos. The number of cells and the number of embryos showing stained PGCs in the gonads was inversely proportional to the age of the PGCs culture.

PGC Transfer Into Recipient Embryos

For PGC transfer, the recipient egg was positioned horizontally under a dissecting scope. A small hole was pierced into the air space of the egg to lower the internal pressure of the egg and prevent leakage. A 10 mm window was opened on the ventral surface of the egg and ~1 ml of PBS with 4% antibiotic/antimitotic was injected through the hole to bring the embryo up until it was slightly less than flush with the egg shell window. To inject the PGCs, a 30 µm pipet was beveled and then pulled using a microforge to form a fine point with polished edges. Two hundred PGCs per embryo transfer, dissociated as described below, were picked up manually using a needle-pipette and a suction tube. Prior to transfer, and while in the pipette, PGCs were mixed with a 0.04% solution of trypan blue stain. The total injection volume per embryo was 2 μl. For the final step, the recipient embryo was positioned to reveal a portion of the marginal vein. The needle-pipette with the PGCs was inserted and the contents carefully expelled. The needle-pipette was held in place for a few seconds and then removed. Recipient eggs were sealed with 2 layers of surgical tape followed by paraffin wax coating of the entire area. Recipient eggs were then placed back into a rotating incubator and incubated until hatching.

Evaluation of the PGC Phenotype

Chicken PGCs are positive for periodic acid Schiff staining (PAS) and are claimed to be positive for alkaline phosphatase. However, there is no convincing evidence that chicken PGCs are positive for the latter. In the absence of an alternative enzymatic or molecular marker method to characterize chicken PGCs, their phenotype was evaluated by transferring cells to recipient embryos and evaluating their presence in the gonads of the developing embryo. This method required culturing the PGCs in 100 μg/ml DiI in a α-MEM medium and rinsing prior to transfer to recipient embryos. Twenty-four hours post-transfer recipient embryos were removed and placed under an inverted microscope. DiI labeled cells observed in the gonads were interpreted as successful PGC migration to the gonads and confirmation of retention of PGC characteristics. A second method to evaluate the retention of the PGC phenotype was pursued by letting recipient embryos go to hatching and then evaluate the presence of donor PGCs in their gonads after breeding.

Breeding Strategy for PGC Evaluation

Two breeding strategies were followed. The first strategy used recipient black feathered birds with possible genotype i/i, E/E, s/s, b/b and donor white feathered broiler type birds with genotype I/I, E/E, S/S, B/B. To prove that recipient animals were chimeric, that is to say that contain their own PGCs and donor PGCs in their gonads, they were mated to pure black feathered birds. If the resulting progeny was all black feathered then the animal was assumed to be non chimeric. However, if some of the progeny was white feathered with some black feathered patches then the recipient animal would be chimeric. For the second breeding strategy Bar Rock birds were used as recipient embryos while white feathered broiler type birds were continued to be used as donors. In this latter case when putative chimeric birds were mated to pure Bar Rocks, the presence of white feathered progeny with some barred feathers would identify a positive chimeric bird. Fifty progeny were obtained from each putative chimeric bird before concluding on its chimeric status.

Progeny Tests

Putative chimeric E/–(WB) birds when crossed to WB birds produced pure white chicks when they originated from a donor (WB) PGC and, white with black speckled feathers chicks when they originated from the (E/–) PGC. Similarly, when BR(WB) were crossed to WB birds. pure white chicks were produced when originating from a donor (WB) PGC and white-speckled black chicks when they originated from a (BR) PGCS. Crosses between putative BR chimeric birds were also done. For the latter, white chicks were produced when fertilization between two (WB) PGCs occurred and black chicks were the result of fertilization with two (BR) PGC. The intermediate white chick with speckled black feathers only happened when a (BR) PGC was fertilized by a (WB) PGC.

Long-Term Cultures Beyond 25 Days

After 25 days of continuous cultures, PGC clumps form rapidly spreading monolayers. These monolayers of cell shave a flat adherent base and looser clumps and chains of PGC like cells on the upper surface. Some packets of these monolayers of cells remain PAS positive. DiI stained cells obtained from these monolayers have been transferred to recipient embryos. Some embryos have shown few cells localized in their gonads. Cell monolayers have been passaged successfully. Generally, these cells are capable of undergoing 3 to 5 passages before they start to slow down their proliferation, age and become fibroblastic looking. There are few cell lines that have gone through multiple passages and continue to thrive without apparent differentiation for about four months in continuous culture.

Two cells lines obtained from monolayers, P102896 and P110596, have been frozen. The former did not show apparent differentiation and was marginally positive for alkaline phosphatase while the latter showed neuronal cell morphology and was strongly positive for alkaline phosphatase. Further characterizations of PGC monolayers as described here remain to be assessed for totipotency and pluripotency.

Summary of Results

Chimeric chickens were generated from fresh and cryopreserved PGCS. Twenty-five (74%) out of 34 putative chimeric chickens, produced with fresh PGCs transfers, proved to be true chimeric animals after progeny testing. Thirty (88%) out of 34 putative chimeric birds, produced with cryopreserved PGCs, were demonstrated to be true chimeric chickens. In all cases, at least 40 progeny were produced and the number of donor PGCs that were fertilized per chimeric bird varied from 1.4% to 100%, with the majority ranging between 30% to 60%. Assuming that the latter is a reflection of the number of PGCs that migrated to the gonad after injection, then the range of success per injection was varied. However, other mechanisms might be operating that might impact the number of PGCs that become established in the recipient gonad. Such mechanisms were not evaluated in this study. Also, on average, we did not observe any significant alteration of sex ratio in the progeny of chimeric birds.

PGC Culture Conditions

None of the cell feeder layers evaluated in this study improved the long term culture conditions of the PGCS. None of the growth factors alone, at any of the concentrations studied, was able to sustain PGCs in vitro without differentiation. Combinations of two and three growth factors were also tested with little success. Based on our results, it appears that all of the factors described above (LIF, BFGF, IGF and SCF) are required for long term culture of PGCS. We are still testing different concentrations and combinations of the above mentioned growth factors in an effort to define the best possible conditions for long term culture of PGCS. Based on DiI staining of PGCs we have observed that, under our culture conditions, PGCs originating from 14 day old continuous cultures migrate to the gonads of recipient embryos alter injection. We have also transferred PGCs that have been maintained in culture for 25 days to three recipient embryos. One of these embryos was chimeric as demonstrated by progeny testing.

PGC Phenotype Under Long Term Culture Conditions

After collection, PGCs are recognized by their size and by the presence of libid droplets in their cytoplasm. At about 48 hours after collection, PGCs clump together and start dividing as evidenced by the growth in size of the clump and the number of cells observed after trypsin dissociation of the clump. Only PGCs that form clumps survive, all others die. Generally, a culture starting with 100 PGCs would end up with an average of 600 to 800 PGCs within seven days. Clearly some PGCs divide, albeit not at an efficient rate. However, as indicated above, these PGCs maintain their ability to migrate to the gonads.

Long-Term Cultures Beyond 25 Days

After 25 days of continuous cultures, PGC clumps form rapidly spreading monolayers. These monolayers of cells have a flat adherent base and looser clumps and chains of PGC like cells on the upper surface. Some packets of these monolayers of cells remain PAS positive. DiI stained cells obtained from these monolayers have been transferred to recipient embryos. Some embryos have shown few cells localized in their gonads. Cell monolayers have been passaged successfully. Generally, these cells are capable of undergoing 3 to 5 passages before they start to slow down their proliferation to age and become fibroblast-like in appearance. There are few cell lines that have gone through multiple passages and continue to thrive without apparent differentiation for about four months in continuous culture.

Two cell lines obtained from monolayers, P102896 and P110596, have been frozen. The former did not show apparent differentiation and was marginally positive for alkaline phosphatase while the latter showed neuronal cell morphology and was strongly positive for alkaline phosphatase. Further characterization of PGC monolayers as described here remains to be assessed for totipotency and pluripotency.

In particular, it has been shown that PGCs cultured using the above four growth factors for at least 25 days can successfully colonize the gonads and produce chimeric chickens. Also, we have maintained PGC cells in culture for up to four months. These cultures still appear to comprise cells having the desired PGC phenotype. While these cells were not tested for their ability to produce chimeric birds, based on their appearance, it is expected that they should be useful therefor.

PGC Transfection

Lipofection of a vector containing the green fluorescence protein reporter gene has been used for transfection of PGCS. On average 1/50 PGCs were transiently transfected, however, no stable transfected cell line has been developed yet.

In summary, these results indicate that PGCs can be maintained for long periods and successfully used for the production of chimeric birds. Further changes on growth factor(s) concentrations and the use of other growth factors may further optimize culturing conditions. To be useful, a PGC culture system should allow for transfection and selection of PGCs while maintaining the PGC ability to migrate to the gonads. Also, as disclosed in more detail in a related application (filed on even date), chicken PGCs, after prolonged culturing, revert to the ES cell phenotype, as occurs with mouse PGCs (Matsui et al., *Cell,* 70: 841–847, 1992). Therefore, injection of dispersed ES cells into recipient blastoderms should provide another means for the generation of chimeric and transgenic chickens.

What is claimed is:

1. A culturing method which provides for maintenance of avian primordial germ cells for periods of at least fourteen days in tissue culture comprising the following steps:

(i) isolating a pure population of primordial germ cells from a desired avian; and (ii) culturing said isolated, pure population of primordial germ cells (PGCs) in a culture medium containing at least the following growth factors contained in amounts sufficient to maintain said PGCs for at least fourteen days in tissue culture:
 (1) leukemia inhibitory factor (LIF),
 (2) basic fibroblast growth factor (bFGF),
 (3) stem cell factor (SCF) and
 (4) insulin-like growth factor (IGF).

2. The method of claim 1, wherein the minimal amounts of said growth factors are:
 (1) LIF (0.00625 U/$\mu$l),
 (2) bFGF (0.25 pg/$\mu$l),
 (3) IGF (0.5625 pg/$\mu$l), and
 (4) SCF (4.0 pg/$\mu$l).

3. The method of claim 2, wherein the maximal amounts of said growth factors range from about two times to one hundred times said minimum amounts.

4. The method of claim 1, wherein said avian PGCs are obtained from an avian of the genus Gallinacea.

5. The method of claim 4, wherein said PGCs are chicken PGCs or turkey PGCs.

6. A method of producing chimeric avians which comprises:

(i) isolating a pure population of primordial germ cells from an avian;

(ii) maintaining said isolated, purified PGCs in a tissue culture medium containing at least the following growth factors;
 (1) leukemia inhibitory factor (LIF),
 (2) basic fibroblast growth factor (bFGF),
 (3) stem cell factor (SCF) and
 (4) insulin-like growth factor (IGF);

(iii) transferring said PGCs into a recipient avian embryo of the same species as the avian used to obtain said isolated, purified PGCs;

(iv) allowing said recipient avian to develop into a bird, and (v) selecting for chimeric avians which express the PGC phenotype.

7. The method according to claim 6, wherein said PGCs are derived from avian embryos of the genus Gallinacea.

8. The method according to claim 7, wherein said avian embryos are turkey or chicken embryos.

9. The method according to claim 6, wherein the PGCs are injected into the dorsal aorta and/or marginal vein of a recipient avian embryo or into recipient blastoderms.

10. A culture consisting essentially of purified isolated avian PGCs contained in a culture medium which comprises growth factors in amounts sufficient to maintain said PGCs for at least fourteen days in tissue culture, wherein said culture medium comprises at least the following growth factors: (1) leukemia inhibitory factor (LIF); (2) basic fibroblast factor (bFGF); (3) stem cell factor (SCF); and (4) insulin-like growth factor (IGF).

11. The culture of claim 10, wherein said avian PGCs are of the species Gallinacea.

12. The culture of claim 10, wherein said avian PGCs are chicken or turkey PGCs.

* * * * *